United States Patent [19]

Schimel

[11] 4,401,565
[45] Aug. 30, 1983

[54] SYSTEMS FOR THE TREATMENT OF ORGANIC MATERIAL AND PARTICULARLY SEWAGE SLUDGE

[76] Inventor: Keith A. Schimel, 200 Ulster St., Apt. 1, Syracuse, N.Y. 13204

[21] Appl. No.: 155,265

[22] Filed: Jun. 2, 1980

Related U.S. Application Data

[62] Division of Ser. No. 3,167, Jan. 15, 1979, abandoned.

[51] Int. Cl.$^3$ ................................................ C02F 11/04
[52] U.S. Cl. .................................... 210/258; 210/522; 210/539
[58] Field of Search ............... 210/180, 188, 218, 258, 210/522, 539, 603, 613, 630

[56] References Cited

U.S. PATENT DOCUMENTS

| | | | |
|---|---|---|---|
| 1,757,263 | 5/1930 | Sims | 210/188 X |
| 2,029,702 | 2/1936 | Buswell et al. | 210/603 |
| 2,195,408 | 4/1940 | Dowhes | 210/188 X |
| 2,786,025 | 3/1957 | Lamb et al. | 210/613 |
| 4,198,292 | 4/1980 | Snider et al. | 210/603 |

Primary Examiner—Thomas G. Wyse
Attorney, Agent, or Firm—Martin LuKacher

[57] ABSTRACT

Anaerobic digestion of organic material, particularly biological sludge, such as sewage sludge, is carried out in a closed system having a first digestion tank and a second concentration and partial digestion tank. The concentrated and partially digested sludge is fed to the first tank where it is maintained under vacuum such that an active zone of organic material undergoing digestion is detained therein for a long period of time. The digested sludge is withdrawn against the vacuum and has approximately 80 to 90% of the organic solids therein mineralized; thus simplifying dewatering and ultimate disposal of the sludge. Pathogens including viruses are also removed from the digested sludge. Denitrification takes place in the vacuum digester tank and gas consisting essentially of nitrogen is removed. Return sludge from the vacuum digester and influent sludge is fed into the second or concentrator tank to facilitate reseeding with anaerobic organisms. Both tanks are provided with passageways which are coterminous near the upper ends of the tanks and provided with baffles which direct the flow to be in opposite directions in the passageways, thus providing for stripping of the gas and solid-liquid separation. Gas consisting essentially of methane and carbon dioxide is produced from the second tank. Supernatant from the second tank may be recirculated to the source of the sludge to facilitate degradation of remaining organic contaminants.

5 Claims, 5 Drawing Figures

SYSTEMS FOR THE TREATMENT OF ORGANIC MATERIAL AND PARTICULARLY SEWAGE SLUDGE

DESCRIPTION

This is a division of application Ser. No. 3,167 filed Jan. 15, 1979, abandoned.

The present invention relates to a system of and method for sewage treatment, and particularly to anaerobic digestion of sewage sludge or other organic material.

The invention is especially suitable for use in the treatment of waste water for hygienic disposal, as in municipal sewage treatment plants, and provides methods and means for the digestion of sludge which is generated in the course of such treatment.

Of the various approaches to sewage treatment, anaerobic digestion has become an important portion of the treatment facilities. A review of anaerobic sludge digestion may be found in *Manual of Practice No. 16-Anaerobic Sludge Digestion*, published by the Water Pollution Control Federation, Washington, D.C. (1968), and in Document EPA 430/9-76-001 entitled *Operations Manual Anaerobic Sludge Digestion*, published by the United States Environmental Protection Agency (1976) and available through the National Technical Information Service, Springfield, Va. and in articles found in the Water Pollution Control Federation Journal, Vol. 26, p. 462–476 (1954), Vol. 27, p. 121–133 (1955), and Vol. 31, (II) p. 164–190 (1959).

Anaerobic digestion as presently practiced has disadvantages. Principal among these disadvantages is that the reduction in volatile organic material is not nearly complete. Only about 40% of the volatile solids are removed and the stabilized (also known as mineralized) sludge obtained from the digester typically has 60% volatile solids as measured by the conventional sludge solids tests (see the above referenced Manual EPA 430/9-76-001, page E9 et seq). Another disadvantage is the hydraulic detention time that the liquid stays in the conventional anaerobic digestion system. Unless the digester is heated, the residence time in the digestor is typically 40 to 60 days. Intermittent or batch feeding and withdrawal further complicate the efficiency of sludge processing. Digesters are sensitive to failure and may become "sour", in which case the entire system must be stopped and the digester tank cleaned out and restarted. The environmental effects of such failures may be serious, particularly where other facilities for treatment are unavailable and raw sewage or untreated sludge must be disposed of into the environment. Some thoughts have been reported on increasing the reaction rates in digestion of volatile acid liquids which are retained without flow resident in a tank under vacuum at one end (see Science, Dec. 12, 1975, p. 1088). However, continuous processing for biological conversion of solid, rather than liquid to final stabilized material and gases has not been suggested heretofore.

Nitrogenous compounds are contained in sewage sludge and complex processes have been proposed for denitrification (see *Final Report—Evaluation of Municipal Sewage Treatment Alternatives*, prepared for the Council in Environmental Quality, Executive Office of the President, in Association With the Environmental Protection Agency, Office of Planning and Evaluation (February 1974), which may be obtained from the Superintendent of Documents, U.S. Government Printing Office, Washington, D.C., pages A-62 through A-84). Such processes require complex and expensive facilities, and have not been generally adopted. The present invention has as one of its features and advantages the denitrification of organic material such as sewage sludge, anaerobically, while the material is treated continuously, and at higher rates than with conventional anaerobic digestion processes. Such conventional processes do not produce nitrogen, but are limited to the generation of methane, carbon dioxide and mercaptans.

While sludge obtained from conventional anaerobic digestion tanks is relatively free of bacterial pathogens, viruses are normally present in digested stabilized sludge. The method and system of anaerobic digestion provided in accordance with the invention has been discovered to provide digested stabilized sludge which may be free of pathogenic viruses as well as bacteria, to the extent that viral testing has been performed up to the present time.

In U.S. Pat. No. 1,757,263, issued to T. B. Sims, on May 6, 1930, and in U.S. Pat. No. 2,029,702, issued to A. M. Buswell, et al, on Feb. 4, 1936, there are disclosed systems for anaerobic digestion of waste organic solids which operate with highly concentrated feed stocks of such solids. Such systems have a solids retention time, approximately equal to their hydraulic retention time and operate intermittently. They suffer from the problem of rapid reaction rates of the acid forming anaerobes. These organisms digest the easily biodegradable carbohydrates and amines to produce high organic acid concentration within the digester. The pH falls and the methane former organisms cease high activity. Digestion falls and the result is a sour reactor. The Buswell system attempts to recycle, intermittently, excess supernatant from a second stage back to a first stage to dilute the rapid acid production to within the pH range where the methane formers remain active. Sims recycles active solids which settle to the bottom of the digester by lift pumps. In both the Sims and Buswell systems, the process is intermittent and the digesters are fed intermittently. Lime is applied in an effort to control the process. Neither the Buswell nor Sims systems solve the problems of (a) separating solids from the processed effluent; (b) nearly completely converting volatile solids to stabilized form; (c) controlling the quality of the anaerobic reduction process in the digester such that acid formation does not affect the process; and (d) producing an output gas having a high content of methane and low content of carbon dioxide and sulfur containing organic gases such as hydrogen sulfide which produces intolerable odors in the anaerobic process.

Separation of the solids from the effluent from the digesters in the Sims and Buswell systems is caused by the highly concentrated digester feed stocks which enhance the production of gas per unit volume of material in their digesters. Consequently the probability increases that a large number of particles exist that had not completed gas transfer from the solid particle to the gas phase. In other words, these particles still have gas attached and their buoyancy causes the particles to float rather than to settle by gravity, and the particles leave the digester in the effluent. Attachment of gas bubbles slows digestion by covering large areas of the biodegradable solids and thereby slows the diffusion processes to active organisms as well as diffusion of metabolic byproducts away from the active organisms. This problem is of particular consequence with organic gases such as methane which has low solubility in water and affinity for the organic solid phase. Mixing as in Sims' system creates further problems in that biochemically active organisms may be sheared from the floc particle, thus producing a discontinuity between the organisms and their substrates. Heavy vacuums, as in the Sims system, affect the biochemistry of the organism and slow digestion. Increasing the temperature to the thermophillic range as in the Buswell et al system aggravates the problem of adhering gases by lowering the solubility of the gases, thereby lowering the diffusion of the gas away from the particles. The Sims and Buswell system thus result in a high concentration of active sludge solids in the processed effluent, loss of digestible carbon, lower process efficiency, loss of active anaerobic organisms, and an extremely odorous effluent. It is a feature of this invention to contain the active organisms within the digesters so that the residence time of the liquid in the digesters (the hydraulic residence time) is short, while the solids residence time is long and the production of an active biomass (active sludge) is minimized.

The conversion of volatile solids in the Sims and Buswell et al systems is not nearly complete. Such systems normally obtain only 10 to 20% sludge volatile solids conversion. The sludge released from processors carried out by the Sims and Buswell et al systems contain only 40% less volatile material then the influent as measured by the standard sludge volatile solids test mentioned above. This low reduction in volatile solids in processes typical of the Sims and Buswell et al systems results from nutrient inhibition due to the failure to remove the usually excessive proportions of nitrogen in the influent to the digester. Digestion of organic solids proceeds until easily biodegradable carbohydrates and amines are removed. Thereafter, digestion only proceeds very slowly, if at all. For this reason digested sludges from processes as in the Sims and Buswell et al system contain a considerable amount of organic material (volatile solids) composed principally of nitrogenous compounds, mainly proteins. These volatile solids rich sludges present problems of handling and disposal. It is a feature of this invention to obtain 80% to 90% sludge volatile solids conversion. The invention provides for the removal of nitrogen in the digester. The overall results of the invention is to substantially solve the problem of handling and disposal of digested solids.

In systems of the Sims and Buswell et al type, control of the problem of high organic acid concentration within the digester is not satisfactorily resolved by means of the solutions proposed therein. The large fraction of volatile acids with high effluent oxygen demand contained in the effluent of such prior art systems is indicated in Table III of the Buswell et al patent. The high concentration of these lower fatty acids in the effluent, typically resulting from systems of the Sims and Buswell et al type, result in organic concentrations in the effluent having a high biochemical oxygen demand. If recirculated to a typical aeration basin, such an effluent causes organic overload, eventual process failure, and the need to dispose an environmentally damaging effluent to the surrounding ecology. Since systems of the Sims and Buswell et al type have a hydraulic residence time which is approximately equal to the solid residence time in the digester, the available liquid volume for dissolving the gases is minimal and the rate of production of odor type gases and carbon dioxide, rapidly overcomes the available dilution capacity of the liquid volume, thus contaminating the process product gas phase. Gas output of systems of the Sims and Buswell et al type normally contains 60% to 65% methane, approximately 35% carbon dioxide, and 1% to 2% hydrogen sulfide. The presence of the organic sulfur gases is highly odorific and renders the products unacceptable as a fuel for internal combustion engines because the hydrogen sulfide in the presence of water vapor combusts to sulfuric acid which dissolves metal structures and leaves the combustion chamber as sulfur oxide pollutants. It is a feature of the invention to provide a controlled process which is continuously operating and which produces a gas composition which presents a substantial improvement over the gas composition produced by the prior art digestion systems of the type described in the Sims and Buswell et al patents.

Accordingly, it is an object of the present invention to provide an improved system for treatment of organic materials such as sewage sludge by biological processes.

It is another object of the present invention to provide an improved system for anaerobic digestion of organic materials and particularly sewage sludge.

It is further object of the invention to provide an improved system for anaerobic digestion in which the reduction in volatile solids contained in the digested and stabilized material is reduced from approximately 40% to 60%, as in the case of conventional anaerobic sludge digestion, to 80% to 90% or more of the volatile solids in the influent material which is treated.

It is a still further object of the invention to provide an improved system for anaerobic digestion of sewage sludge in which digestion time is reduced, such that the hydraulic loading or residence time of the liquid in the system is reduced substantially from the hydraulic loading or residence time in the case of conventional anaerobic sludge digesters, and continuous feeding of influent and withdrawal of effluent digested sludge is made feasible.

It is a still further object of the present invention to provide an improved system for anaerobic digestion of sewage sludge which is continuous in operation rather than intermittent or batch operated.

It is a still further object of the invention to provide an improved system for anaerobic sludge digestion which enables the continuous removal of digested (viz stabilized or mineralized) sludge.

It is a still further object of the present invention to provide an improved system for anaerobic digestion of sludge in which digestor failure possibilities are reduced and the consequent need for shut-down, clean-out, and restarting of the digestor is minimized.

It is a still further object of the invention to provide an improved system for anaerobic digestion of sewage sludge whereby the sludge is disinfected of pathogenic bacterial and may also be disinfected of pathogenic viruses.

It is a still further object of the present invention to provide an improved system for anaerobic digestion of organic materials such as sewage sludge which denitrifies the material and provides a source of nitrogen.

Briefly described, the system for the treatment of slurries of organic material, such as sewage sludge, in accordance with the invention makes use of a tank in which anaerobic conditions are established. By means of pumps associated with the tank, regions below atmospheric pressure are provided at opposite ends of the tank. The material to be treated may be any biological sludge, such as activated sludge, and preferably is partially digested and concentrated sludge from another tank in which concentration and anaerobic digestion takes place and which is connected to the first mentioned tank in a closed system. The sludge is fed continuously and preferably through the closed system into the tank which is at vacuum. The rate or velocity of feeding is such that an active zone containing a suspension of solids of the organic material is formed in the tank. As the material stabilizes, it falls to the bottom of the tank and is drawn off as by a pump. Gas in the form of nitrogen is stripped from the liquid material as it circulates through the tank. Baffles disposed at the end of passageways formed in the tank for the flow of the liquid are preferably used to facilitate the stripping of the gas. The gas removed consists essentially of nitrogen. The digested sludge has a high content of stabilized material with volatile solids reduced to fro 40% to at least 80% of the volatile solids contained typically in influent sewage sludge from a source such as an aerobic mixing tank of a secondary treatment system. The digested sludge has been found to be essentially free of pathogens including viruses.

The foregoing and other objects, features and advantages of the invention as well as the best mode now known for practicing the invention and a preferred embodiment thereof will be more apparent from a reading of the following description in connection with the accompanying drawings in which.

Figure 1:
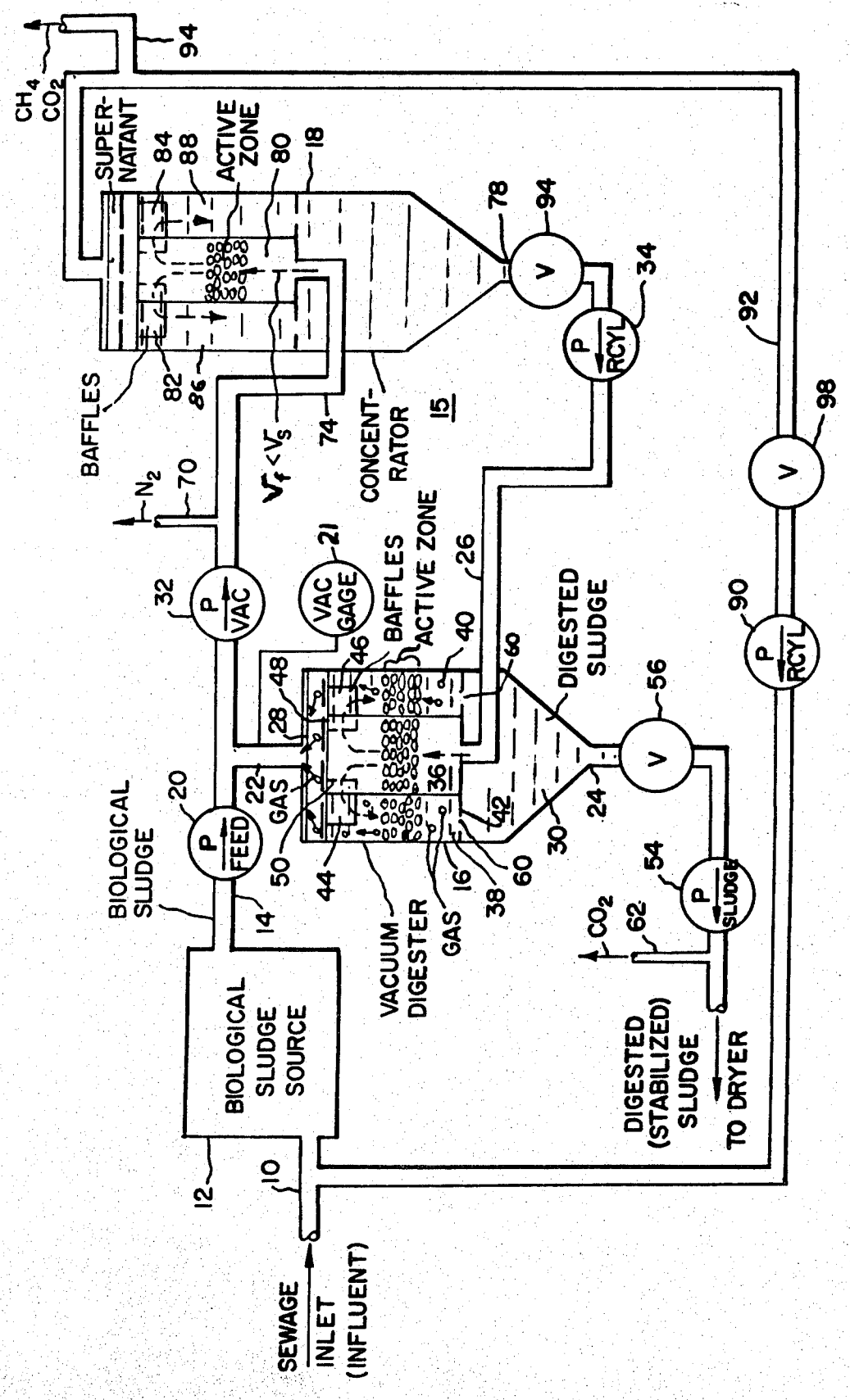
FIG. 1 is a diagram schematically showing an anaerobic sludge digestion system in accordance with the invention.
Figure 2:
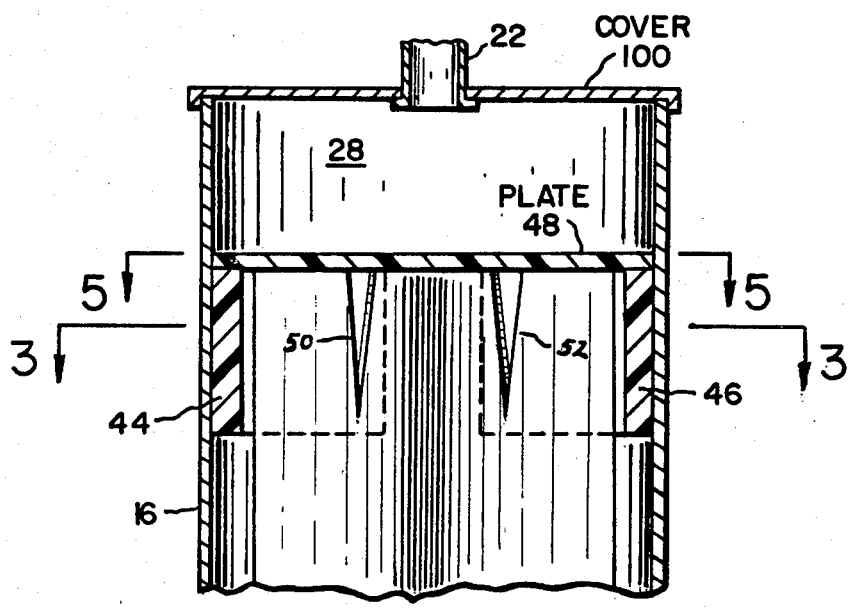
FIG. 2 is a fragmentary view in elevation of the upper portion of one of the tanks in the system of FIG. 1.
Figure 3:
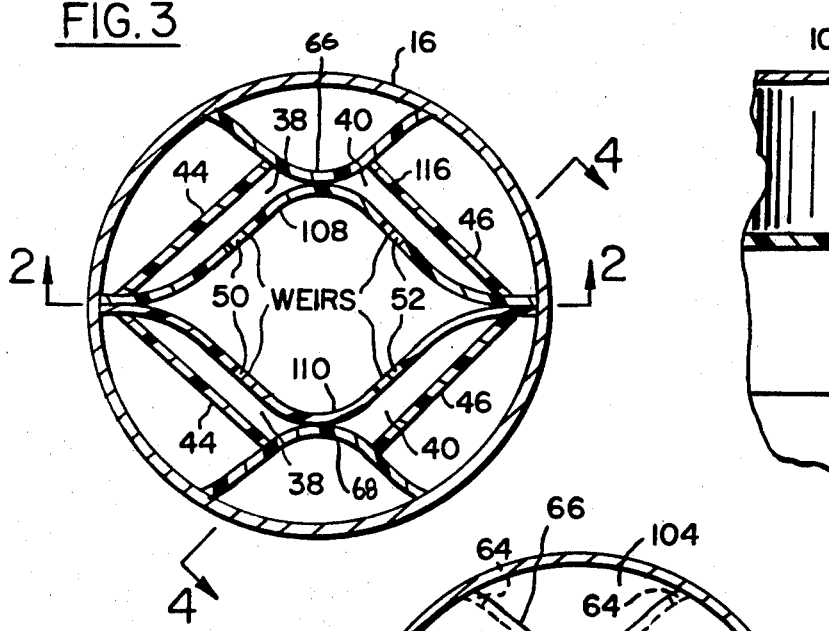
FIG. 3 is a sectional plan view of one of the tanks, the view being taken along the line 3—3 in FIG. 2.
Figure 4:
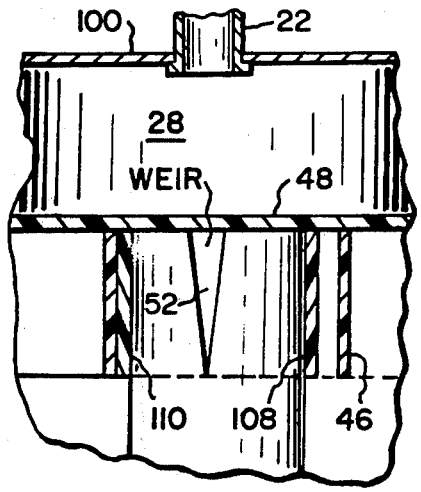
FIG. 4 is a fragmentary sectional view of one of the tanks, the view taken along the line 4—4 in FIG. 3.

Referring more particularly to FIG. 1, there is shown a biological sludge source 12. The source 12 may be waste sludge from a biological treatment unit, such as a primary clarifier sludge, activated sludge, trickling filter waste sludge and the like. For example, sewage which has preferably undergone primary treatment to remove grit is fed into an inlet 10 and into a secondary treatment system which may include the conventional clarifier, such as filters or sedimentation chambers and aerator tanks which provide the source of biological sludge. This sludge may be activated sludge. This source 12 is shown diagrammatically in FIG. 1. The output from the source is obtained from an outlet 14 near the top of a tank and is fed continuously into a closed loop system 15 containing two tanks 16 and 18 in which anaerobic digestion of the sludge takes place. A pump 20 which may suitably be of the constant displacement type feeds the sludge into the closed loop system 15. The tank 16, which is referred to herein as the vacuum digester, outputs digested (viz. stabilized and mineralized) sludge and elutriation liquor. This digested sludge may be filtered or further purified. This sludge contains liquid high in ammonia and may alternatively be used as a fertilizer and applied to the land. The tank 18 is referred to as the concentrator.

The tanks 16 and 18 and the lines interconnecting them are preferably constructed of material which is non-biodegradable. In small scale systems, acrylic plastic material may be used.

The vacuum digester tank 16 has outlets 22 and 24 at opposite ends thereof. The tank 16 is preferably maintained with its longitudinal axis vertical. The lower end of the tank may be conical in shape. The tank 16 is also provided with an inlet 26 for the concentrated and partially digested sludge from the concentrator tank 18. This inlet enters the tank 16 between a region 28 at the top of the tank and a region 30 at the bottom of the tank. The pressure in the top region 28 is below atmospheric pressure and is a vacuum. The vacuum is maintained by a pump 32 which is operated at a faster rate than the feed pump 20. A gauge 21 measures the vacuum pressure of about $-50$ centimeters of mercury (gauge pressure) has been found suitable. The optimum vacuum range is between $-30$ to $-50$ cm Hg gauge vacuum. The amount of vacuum needed to maintain the solids in suspension is dependent on the character of the solid (i.e., the solid biodegradability).

The concentrated sludge from the concentrator tank 18 is fed into the inlet 26 of the vacuum digester tank 16 by a pump 34, which may also suitably be a constant displacement pump. In the tank 16, partitions form a plurality of passageways between the bottom and top regions 30 and 28 of the tank 16. A central passageway 36 and two passageways 38 and 40 which are adjacent thereto, are shown in FIG. 1. A plate 42 with holes 60 therethrough, is disposed at the bottom of the passageways and an arrangement of baffles 44 and 46 attached to an upper plate 48 are disposed at the top of the passageways 36, 38 and 40.

The concentrated sludge from the inlet enters through the bottom plate 42 into the central passageway 36. The liquid in the sludge flows in the direction shown by the arrows on the dash lines through openings 50 and 52 (see FIGS. 2 to 5). These openings 50 and 52 are in the form of weirs at the partitions between the center passageway 36 and the passageways 38 and 40 adjacent thereto. The flow against the vacuum is obtained by gravity and by applied vacuum from another pump 54 which withdraws digested sludge and elutriation liquor, which is the effluent from the closed loop 15, from the lower region 30 of the tank 16. This sludge pump 54 may also be a constant displacement pump. The flow and pressure is adjusted by means of a valve 56.

Inasmuch as the sludge source 12 is open to the air and this source 12 is connected to the concentrator tank 18, the concentrator tank and the portion of the system between the vacuum pump 32 and the concentrator tank 18 is at atmospheric pressure. The vacuum digester tank 16 is below atmospheric pressure and maintained at vacuum by the vacuum pump 32. After the system is in operation, all air is withdrawn and anaerobic conditions are established and continue to exist so long as the system is in operation.

The vacuum established in the upper region 28 maintains the volatile organic solids in suspension in an active zone in the passageways 36, 38 and 40, thus concentrating the solid mass. As the solid volume is reduced (stabilized) by microbial action, the incoming solids from passageway 36 fill the void volume thus continuously concentrating the solids in the reactor. While the vacuum and the low specific gravity of the volatile organic solids tends to make them rise, a small vacuum exerted by the sludge pump 54, tends to bring the liquid and mineralized suspended particles downward. The pressures are adjusted such that the volatile organic solids are maintained in the active zone for an extremely long period of time until the action of the anaerobic bacteria stabilizes and mineralizes them. The solids become heavier as mineralization progresses. The increased specific gravity is also due, it is believed, because of gas molecules which have a higher probability of attaching to the volatile organic solids than to the stabilized and mineralized solids. The stabilized and mineralized solids then move downward through the outside passageways 38 and 40, through openings 60 in bottom plate 42 and drop into the conical lower region whence they are withdrawn with the liquid through the outlet 24. A gas outlet 62 for the withdrawal of gas which may be released from the digested sludge is provided at the outlet side of the sludge pump 54.

As the volatile organic materials in suspension in the active zone are digested, gas is released. Further, as the liquid flows through the weirs 50 and 52 at the upper end of the passageways 36, 38 and 40 and is deflected by the baffles 44 and 46, gas is stripped from the liquid. This gas is drawn by the vacuum in the upper region 28 through openings shown as notches 64 in two of the partitions 66 and 68 which form the passageways 36, 38 and 40 (see FIG. 5). The gas has been found to consist essentially of nitrogen ($N_2$) with some methane ($CH_4$) released from time to time in small amounts. This gas may be withdrawn through a gas outlet 70 on the pressure side of the vacuum pump 32.

The exact biological or other process which takes place in the vacuum digester tank 16 so as to release nitrogen gas from the upper outlet 22 and digested sludge of low volatile organic solid content from the lower outlet 24 is not fully understood at the present time.

It is believed that the process of removal of nitrogen is similar to what occurs when synthetic ammonia is produced in the so-called Haber process, because of the vacuum conditions existing in the vacuum digester result in materials therein which have a partial pressure having a greater proportion of their resident molecules in the gas phase than under standard atmospheric conditions. The result is the ammonia-ammonium equilibrium described by the following equations:

$$NH_3 + H_2O \leftrightarrow NH_4^+ + OH^- \quad (1)$$

$$NH_3 + (aq) \leftrightarrow NH_3(gas) \quad (2)$$

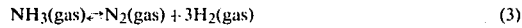

$$NH_3(gas) \leftrightarrow N_2(gas) + 3H_2(gas) \quad (3)$$

It is believed that a reverse Haber process (reaction (3) above) occurs in the digester and is responsible for the nearly complete denitrification observed. This is quite different from the process of denitrifying bacteria in the presence of nitrate and nitrite ions (see Neff et al U.S. Pat. No. 3,994,803 and Miyaji U.S. Pat. No. 3,607,736. The reaction towards the right is favored in the presence of a stable catalyst, since the sludge solid particles are so concentrated and have a widely varying heterogenous mass of both living and non-living materials, the possibilities exist for the actual catalyst which controls the Haber process. Furthermore, the gas bubbles generated are caught in the thick concentrated sludge which is maintained in suspension in the stage 16 maximizing contact between the gas phase and active organisms.

The conditions which result in the operation, namely the vacuum anaerobic condition in the digester tank 16 and the influx and withdrawal of the sludge into the tank continuously have been found, quite unexpectedly, to provide high solids destruction during short hydraulic residence time, typically 30 hours hydraulic loading or residence time in the system, as compared to 40 to 60 days in conventional anaerobic digesters. The system is operated to provide these results at room temperature, approximately 68° F. (20° C. ±1° C.). Higher temperatures may be used. A high concentration of anaerobic organisms, from the upper region 28 of the vacuum digester tank 16, are recycled and mixed with the incoming raw sludge metered through feed pump 20, and applied to the concentrator tank 18 through inlet 10 from the upper region 28 of the vacuum digester tank is applied to the concentrator tank 18 through an inlet 74. The tank 18 also has top and bottom outlets 76 and 78, and is oriented with its longitudinal axis vertical. The bottom of the tank may be conical in shape. The tank also has an arrangement of partitions, plates and baffles, similar to the arrangement used in the vacuum digester tank 16. The influent activated sludge mixture from the vacuum digester tank 16 is fed through a central passageway 80 forming an active zone and is diverted by baffles 82 and 84 into adjacent passageways 86 and 88. The liquid flow is in the direction shown by the arrows. The baffles 82 and 84 assist in stripping the gas which together with the supernatant flows through the outlet 76. The supernatant may be recycled back into the activated sludge unit by means of a recycling pump 90 through the feed lines 92. A gas outlet 94 for the methane and carbon dioxide resulting from the partial digestion of the sludge in the tank 18 is also provided. The velocity of flow of liquid through the passageways 80, 86 and 88 is controlled by means of valves such as the valve 94 between the outlet 78 and the recycling pump 34. The velocity of this flow, $v_f$, is suitably less than the settling rate, $v_s$, for solid particles through water. This settling rate is approximately 2.7 centimeters per second. Slower flows for the liquid may be used but preferably the flow should not exceed the settling rate for solid particles. This enables the solid particles to concentrate both by bioflocculation and sedimentation.

Concentrated and partially digested sludge from the tank 18 is recycled by the pump 34 to the inlet 26 of the digestion tank. A concentration of 6 to 10 times in terms of the solids content of the sludge is obtained in the concentrating tank 18. For example, the influent sludge at the outlet 14 of the source may have a concentration of 2500 milligrams per liter of solids material, while the sludge which is obtained at the outlet 78 of the tank 18 has a concentration of 12,000–30,000 milligrams per liter approximately. This tank is maintained at approximately atmospheric pressure.

The system operates continuously with the rates of flow adjusted such that the digested and stabilized sludge content in terms of volatile solids is 80% to 90% less than the volatile solids in the activated sludge influent obtained at the outlet 14 of the source 12. In the event that the volatile solids concentration varies, the rates of flow are adjusted by means of the valves 56 and 94. In the event that the recycling of the supernatant from the top of the concentrator tank 18 is used (such recycling is optional and is desirable when additional dissolved organic contaminant removal is needed), its flow is adjusted by the valve 98. It will be observed that the closed loop affords a feedback signal with error control in terms of the volatile solids content of the digested stabilized sludge. While volatile solids tests may be performed intermittently and adjustments of flow rate made intermittently, continuous testing and automatic adjustment may be implemented through feedback control techniques of the type used in electrical servo systems.

The construction of the passageways and baffling arrangements in the tanks is shown in FIGS. 2 through 5. Considering the tank 16 for example, since the arrangement of passageways and baffles is similar in both tanks 16 and 18, it will be observed that the tank is closed by a cover 100 at the upper end thereof where the outlet is located.

Figure 5:
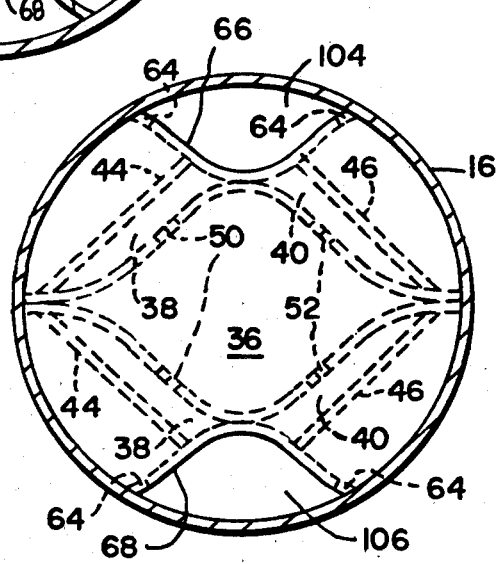
FIG. 5 is another sectional plan view taken along the line 5—5 in FIG. 2.

The plate 48 is disposed below the top of the tank to provide the region 28 for the escape of the gas and active sludge through the outlet 22. This region is maintained at vacuum by the pump 32. The plate has convolute cut-away sections which conform to the shape of the partitions 66 and 68 which form walls of the side passageways 38 and 40. These cut-away sections are indicated at 104 and 106 in FIG. 5. The baffles 44 and 46 extend between the partitions 66 and 68 and partitions 108 and 110 which are convolute in shape and form the walls of the central passageway 36 and the passageways 38 and 40 which are adjacent thereto. There partitions are defined by sheets. The sheets form a honeycomb in cross-section (see FIG. 3) and define the passageways therethrough. In other words the honeycomb is in a plane perpendicular to the length of the passageways. The weirs 50 and 52 are triangular notches in the partitions 108 and 110. The flow of liquid is through these weirs into the passages 38 and 40. Deflection occurs at the baffle plates 44 and 46. Gas which is stripped from the liquid at the baffle plates exits through small notches 64 (FIG. 5). The cover plate 48 and also the bottom plate 42 may be made of acrylic material. The partitions may be made of another non-reactive plastic such as from sheets of polyvinyl chloride. The partitions may be cemented together with epoxy cement or heat welded to form a unitary assemblage.

From the foregoing description it will be apparent that there has been provided an improved method of and system for the anaerobic digestion of organic materials and particularly sewage sludge. While an exemplary form of the system and the best mode now known for operating the system and practicing the method has been described, it will be appreciated that variations and modifications within the scope of the invention and particularly which are designed to obtain the advantages and new results of low hydraulic residence time and loading, the production of nitrogen and the production of digested stabilized sludge of low volatile solids content will undoubtedly suggest themselves to those skilled in the art. Accordingly, the foregoing description should be taken as illustrative and not in any limiting sense.

What is claimed is:

1. The system for digestion of slurries of organic material which is useful for treatment of sewage sludge comprising a tank having outlets communicating with regions at opposite ends of said tank and an inlet means between said regions, means for continuously introducing the material to be treated into said tank via said inlet, means for establishing a pressure differential in said tank between said regions such that said material is maintained in suspension until substantially digested and mineralized and flows into one of said regions, said pressure differential establishing means comprising means connected to the outlet communicating with a first of said regions toward which said material flows from said inlet for establishing a vacuum pressure therein below atmospheric pressure, means for withdrawing said digested and mineralized sludge and gas via said outlets, pump means connected to said inlet means and with the outlet communicating with a second of said regions for continuously introducing said material to be treated and withdrawing against said vacuum said substantially digested material, means in said tank between said regions for providing a plurality of passageways for liquid flow between said regions, said inlet means being in communication with at least one of said passageways such that flow therein is toward said first region, means including baffles at one end of said passageways adjacent to said first region for deflecting liquid to flow in another of said passageways towards said second region thereby promoting the stripping of gas from said liquid, and said passageway providing means comprising a plurality of sheets of material of convolute configuration which define a honeycomb in a plane perpendicular to the length of said passageways, said one of said passageways being disposed longitudinally along the central axis of said tank, a plate disposed over and covering the end of said one passageway and passageways adjacent thereto, said baffles being plates dependent from said covering plate into said adjacent passageways, and wiers in the walls of said one passageway disposed opposite to said baffle plates for the flow of liquid between said on passageway and the passageways adjacent thereto having said baffle plates therein.

2. The system for digestion of slurries of organic material which is useful for treatment of sewage sludge comprising a tank having outlets communicating with regions at opposite ends of said tank and an inlet means between said regions, means for continuously introducing the material to be treated into said tank via said inlet means, means for establishing a pressure differential in said tank between said regions such that said material is maintained in suspension until substantially digested and mineralized and flows into one of said regions, said pressure differential establishing means comprising means connected to the outlet communicating with a first of said regions toward which said material flows from said inlet means for establishing a vacuum pressure therein below atmospheric pressure, means for withdrawing said digested and mineralized sludge and gas via said outlets, a second tank having an inlet for the material to be treated and outlets at opposite ends thereof, means for connecting one outlet of said second tank to said inlet of said first tank and one of said outlets of said first tank which is in communication with said first region to the inlet of said second tank, means feeding influent material to be treated between said one outlet of said first tank and said inlet of said second tank, pump means in said connecting means providing a loop for continuous flow through said tanks, means in said second tank providing for the partial anerobic digestion and concentration of said influent material to provide supernatant and gas consisting essentially of $CH_4$ and $CO_2$ at another of said outlets of said second tank and concentrated material at said one outlet of said second tank which is connected to said inlet of said first tank.

3. The system as set forth in claim 2 wherein said second tank is oriented vertically with said one outlet adjacent to the bottom thereof and said other outlet adjacent the top thereof, means providing a plurality of vertical passageways being connected to said second tank inlet at the lower end thereof, means including baffles disposed adjacent the upper ends of said passageways for deflecting the upward flow of liquid from said central passageway into downward flow through at least one of the other of said plurality of passageways whereby to promote stripping of gas from said liquid, and means for controlling the flow of fluid into and out of said second tank so as to be less than the settling rate of solid particulate components of said influent and enable concentration by settling and bioflocculation.

4. The system as set forth in claim 3 wherein said pump means includes a pump for drawing the vacuum disposed between said one outlet of said first tank and said inlet of said second tank and another pump for circulating the concentrated and partially digested material from said first tank disposed between said one outlet of said second tank and said inlet of said first tank, outlet means for gas between said vacuum pump and said second tank inlet and also at said other outlet of said second tank for removing gas consisting essentially of $N_2$ between said vacuum pump and said second tank inlet and gas consisting essentially of $CH_4$ and $CO_2$ at said other outlet of said second tank.

5. The system as set forth in claim 2 further comprising a source of organic material which provides said influent material, and means connecting said other outlet of said second tank to said source for maintaining said second tank at atmospheric pressure and recycling said supernatant thereto.

* * * * *